United States Patent [19]

Fleischman

[11] Patent Number: 4,777,829
[45] Date of Patent: Oct. 18, 1988

[54] MULTI-STATION PIEZOELECTRIC LOAD CYCLE COUNTER

[75] Inventor: Thomas S. Fleischman, North Canton, Ohio

[73] Assignee: The Firestone Tire & Rubber Company, Akron, Ohio

[21] Appl. No.: 103,780

[22] Filed: Oct. 2, 1987

[51] Int. Cl.$^4$ .............................................. G01N 3/32
[52] U.S. Cl. ...................................................... 73/810
[58] Field of Search ................ 73/808, 809, 810, 811, 73/812, 834, DIG. 4; 310/338

[56] References Cited

U.S. PATENT DOCUMENTS

| | | |
|---|---|---|
| 3,269,175 | 8/1966 | Sprosty ............................ 73/DIG. 4 |
| 3,416,363 | 12/1968 | Siems . |
| 3,441,718 | 4/1969 | Hatherell et al. ...................... 235/92 |
| 3,473,046 | 10/1969 | Wonson ................................. 307/308 |
| 3,474,265 | 10/1969 | Frantz .................................. 307/308 |
| 3,777,555 | 12/1973 | Petrisko et al. . |
| 3,782,184 | 1/1974 | Shuck . |
| 3,826,902 | 7/1974 | Claxton et al. ..................... 235/151.3 |
| 3,969,930 | 7/1976 | Prevorsek et al. . |
| 4,010,679 | 3/1977 | Dybel ..................................... 100/53 |
| 4,030,348 | 6/1977 | Fletcher et al. ................... 73/810 X |
| 4,138,898 | 2/1979 | Dybel ..................................... 73/767 |
| 4,383,449 | 5/1983 | Mickowski ............................ 73/764 |

Primary Examiner—Jerry W. Myracle
Attorney, Agent, or Firm—Ernst H. Ruf

[57] ABSTRACT

A piezoelectric load cycle counter is provided for a multi-stationed strain-life tester. A plurality of test specimens are interposed between a fixed upper bracket and a lower reciprocating bracket and are cyclically flexed therebetween. Piezoelectric crystals maintained in association with the upper bracket with each of the test stations present an output signal on each flexure of the test specimen. These output signals enable a counter which counts the number of cycles of the lower bracket. When a specimen breaks, the output signal of the associated station terminates and the count for that station similarly terminates.

17 Claims, 3 Drawing Sheets

4,777,829

MULTI-STATION PIEZOELECTRIC LOAD CYCLE COUNTER

TECHNICAL FIELD

The invention herein resides in the art of testing apparatus and, more particularly, to a fatigue-to-failure tester used for testing elastomeric specimens and which includes an electronic sensing device for determining the number of flexures of a specimen before failure.

BACKGROUND OF THE INVENTION

Heretofore, fatigue-to-failure testers have been commonly known in industries dealing with elastomeric compounds. Typically, a plurality of elastomeric specimens are placed in such a tester and repeatedly flexed at a selected rate and amplitude until the specimens fail. The number of flexures endured assist in defining important characteristics of the elastomeric material. In known testers, a plurality of test sites or stations are provided, each receiving an elastomeric specimen and cycled in unison. Electromechanical counters are typically associated with each station to count the number of flexure cycles endured prior to failure. The electromechanical counters are so positioned as to be activated by the flexure force. They introduce an additional deflection which must be accounted for in the calibration of the tester and which may lead to mechanical failure of the fixturing.

It is also known that the electromechanical counters of the prior art are subject to mechanical failure and themselves have a finite life expectancy. Accordingly, there is a need in the art for a strain-life or a fatigue-to-failure tester in which the sensing and counting mechanism is not prone to mechanical breakage or inoperativeness.

SUMMARY OF THE INVENTION

In light of the foregoing, it is a first aspect of the invention to provide a multi-station piezoelectric load cycle counter in which the sensing mechanism for counting the number of cycles endured does not deflect.

Still a further aspect of the invention is the provision of a multi-station piezoelectric load cycle counter in which the sensing and counting mechanism is totally electronic, and not given to mechanical breakage.

Still a further aspect of the invention is the provision of a multi-station piezoelectric load cycle counter which may be implemented with state of the art strain-life testers.

Yet an additional aspect of the invention is the provision of a multi-station piezoelectric load cycle counter which is durable and reliable in operation, economical to construct and operate, and conducive to implementation with a large variety of tester systems.

Certain of the foregoing aspects of the invention are achieved by a cycle counter for testing elastomeric specimens, comprising: a stationary bracket; a reciprocating bracket adapted for cyclic reciprocating movement toward and away from said stationary bracket; first circuit means connected to said reciprocating bracket for controlling cycles of said reciprocating movement and presenting a first output signal at each such cycle; a test specimen of elastomeric material interconnected between said stationary and reciprocating brackets, said test specimen being flexed by said reciprocating movement; sensing means maintained at said stationary bracket and interconnected with said test specimen for generating a second output signal corresponding to a force applied thereto through said test specimen; and second circuit means connected to said first circuit means and said sensing means, receiving said first and second output signals, and determining therefrom the number of said cycles endured by said test specimen until failure thereof.

Yet additional aspects of the invention are attained by an elastomeric testing apparatus, comprising: a stationary member, a reciprocating member; a test specimen of elastomeric material interconnected between said stationary and reciprocating members, said test specimens cyclically flexed by reciprocating movement of said reciprocating member; a piezoelectric crystal operatively connected to said test specimen and generating a first output signal as a function of said flexing of said reciprocating member; and circuit means receiving said first output signal and counting a number of cycles said test specimen is flexed until failure of said test specimen.

DESCRIPTION OF THE DRAWINGS

For a complete understanding of the objects, techniques and structure of the invention reference should be had to the following detailed description and accompanying drawings wherein.

BEST MODE FOR CARRYING OUT THE INVENTION

Figure 1:
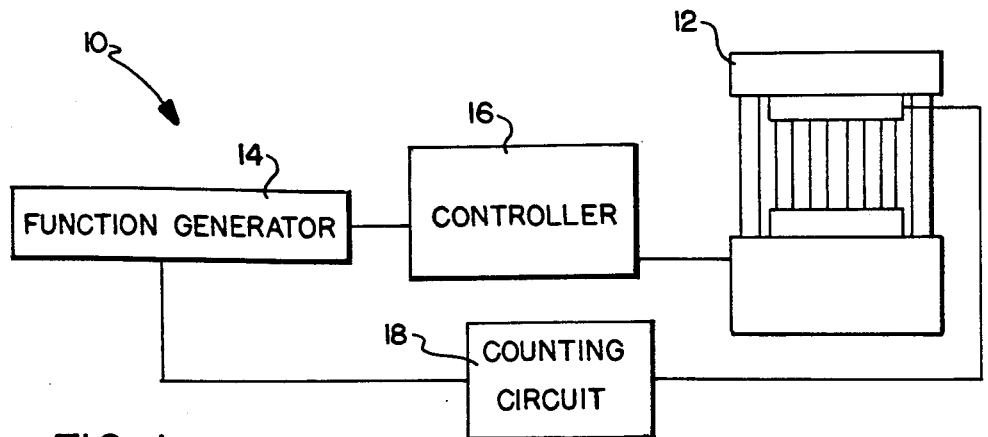
FIG. 1 is a schematic diagram of the invention.

Referring now to the drawings and more particularly FIG. 1, it can be seen that an elastomeric fatigue-to-failure tester or strain-life tester is designated generally by the numeral 10. As is well known in the art, the tester 10 includes a test fixture 12 adapted for receiving samples of elastomeric material therein and which are ultimately longitudinally flexed to failure. A function generator 14, under operator control, generates output signals which establish the amplitude and frequency of the flexures induced into the elastomeric material via the test fixture 12. A controller 16 receives the output signals from the function generator 14 and applies appropriate control signals to the test fixture 12 for controlling the aforesaid amplitude and frequency. Finally, a counting circuit 18 receives a sync signal from the function generator 14 and outputs from the test fixture 12 from which the number of flexure cycles experienced by the elastomeric test material can be counted until the material fails.

Figure 2:
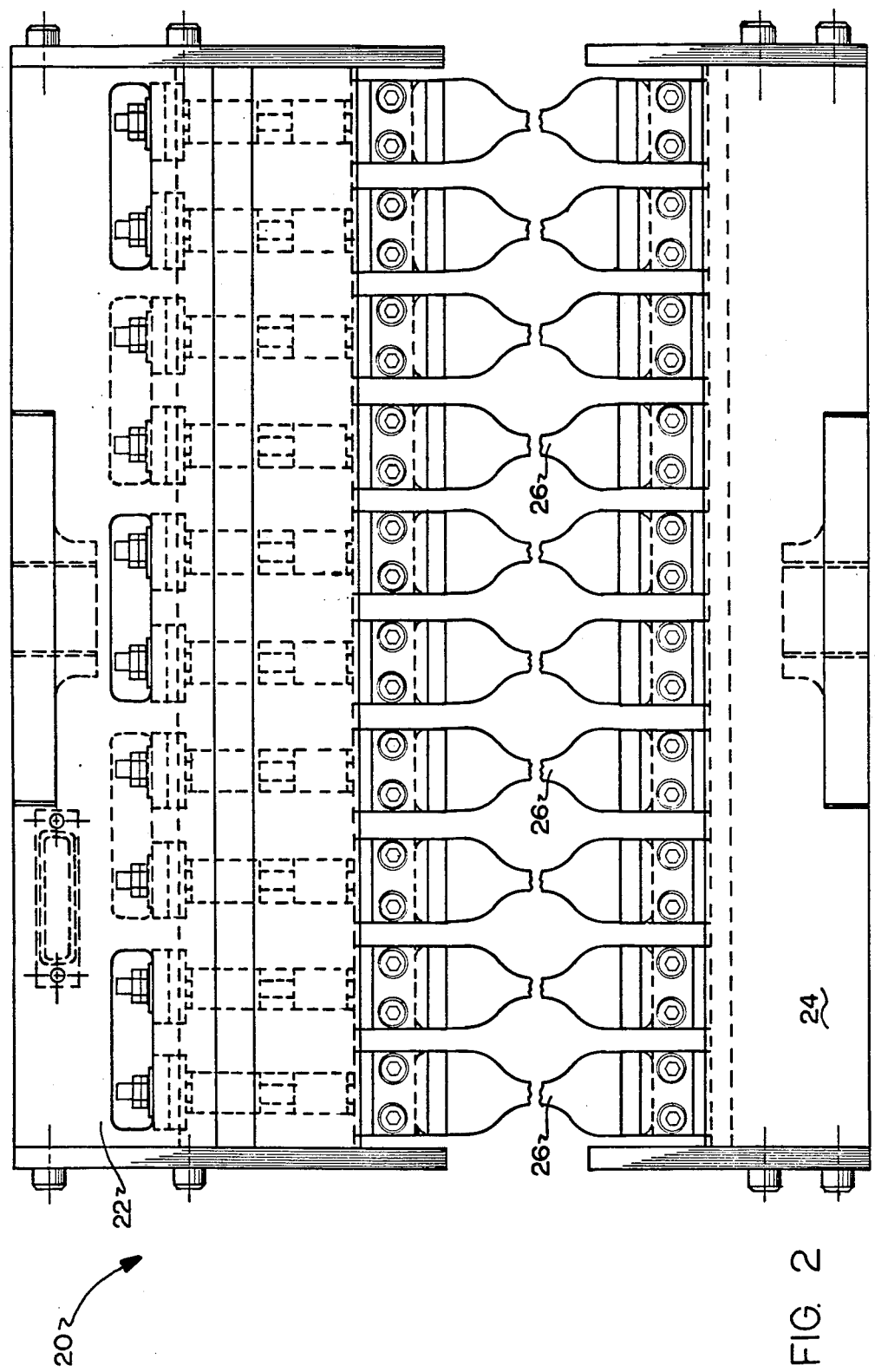
FIG. 2 is a front perspective view of the test head of a strain-life tester according to the invention.

FIG. 2 presents a front perspective view of the test head assembly 20 of the test fixture 12. As shown, the assembly 20 includes an upper stationary bracket assembly 22 and a lower reciprocating bracket assembly 24. Of course, appropriate hydraulic, pneumatic, or mechanical means are provided to achieve the desired reciprocating action. As illustrated in FIG. 2, dumbbell shaped elastomeric specimens 26 are interconnected between the upper and lower bracket assemblies 22, 24 to be flexed by the reciprocating action of the lower bracket assembly 24 to the point of failure. The bracket assemblies 22, 24 are so configured as to receive a plurality of test specimens as, for example, ten.

As is readily known to those skilled in the art, the elastomeric specimens 26, one at each test station, are of a selected nature as to thickness, width, and the like. As discussed above, the amplitude and frequency of the oscillations or reciprocations of the lower reciprocating bracket assembly 24 are controlled by the function generator 14 and controller 16. Of course, the function generator 14 is operator controlled such that a large variety of tests may be performed.

Figure 3:
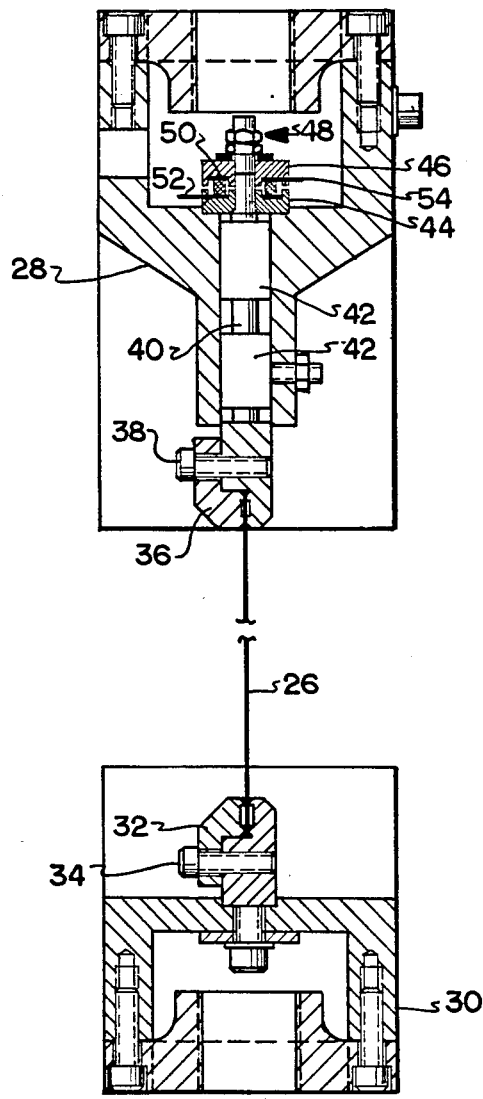
FIG. 3 is a cross sectional view of the test head of FIG. 2.

As shown in FIG. 3, the upper stationary bracket assembly 22 includes an upper bracket 28 opposed from the lower bracket 30 of the lower reciprocating bracket assembly 24. A lower grip 32 is provided with a pair of bolts 34 for purposes of securing a lower end portion of the elastomeric specimen 26. In like manner, an upper grip 36 is provided with a pair of bolts 38 for securing an upper end of such specimen.

A rod 40, connected to the upper grip 36, passes through bushings 42 through which it is adapted for limited reciprocating movement. The other end of the rod 40 passes through a lower insulator 44 which is received by the upper bracket 28. The rod 40 similarly passes through the upper insulator 46, with the end thereof being secured by a nut and washer assembly 48. This secured engagement urges the insulators 44,46 toward each other, and limits movement of the rod 40 independent of the upper insulator 46.

A piezoelectric crystal 50, shaped in the form of an annular disk, is maintained about the rod 40 between the insulators 44,46. As is well known to those skilled in the art, a piezoelectric crystal presents an output voltage signal which corresponds to the force or pressure applied thereto. Accordingly, as the elastomeric specimen 26 is stretched as by downward movement of the reciprocating lower bracket 30, the output signal on the contacts or lead wires 52,54 increases. As the elastomeric specimen 26 is relaxed by upward movement of the reciprocating lower bracket 30, the output decreases such that, typically, as the specimen 26 is flexed, the output of the associated elastomeric crystal 50 is a sinusoidal voltage, passing through one cycle on each cycle of the function generator 14.

It will, of course, be understood that flexing of the specimen 26 induces a force into the piezoelectric crystal 50 which passes from the specimen 26, through the rod 40, the nut and washer assembly 48, and to the upper insulator 46. The upper insulator 46 induces a pressure or force onto the crystal 50 which is maintained upon the stationary lower insulator 44.

Figure 4:
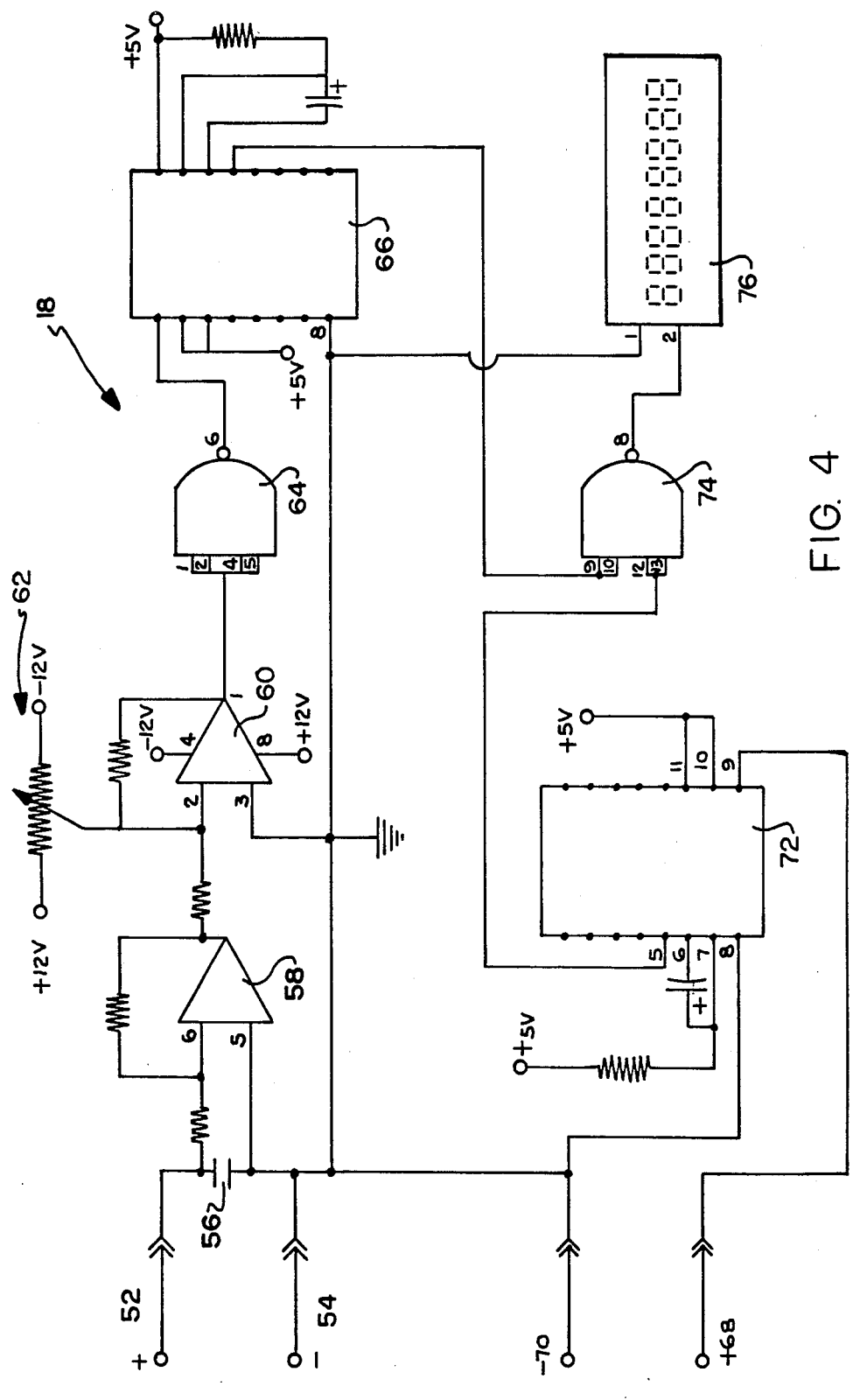
FIG. 4 is an electrical schematic of the circuitry of the invention.

With reference now to FIG. 4, an appreciation of the circuitry of the invention may be obtained. Associated with each of the stations of the test fixture 12 is a counting circuit 18. Of course, it will be understood that certain portions of the counting circuit could be multiplexed between various counting stations, but for purposes of description, it assumed that each such station has its own counting circuit. As shown, this circuit includes a filter capacitor 56 which receives the output signal from the piezoelectric crystal 50 from the leads 52,54. This signal is passed to an operational amplifier 58 which serves to buffer and amplify the input. The output of this amplifier is passed to the operational amplifier 60 which serves to scale the output of the piezoelectric crystal 50 by means of the voltage divider 62. As is readily known to those skilled in the art, such a voltage divider is commonly used to provide a desired offset voltage. As discussed above, it should be readily apparent that the output of the amplifier 60 would typically be a sinusoidal signal which, for purposes of digital analysis, is squared by means of the Schmidt trigger 64. The square wave output of the Schmidt trigger 64 is passed to the monostable multivibrator 66 which is timed such that its output remains high so long as the output of the Schmidt trigger 64 fluctuates between high and low levels. In other words, as long as the output of the Schmidt trigger 64 is a square wave, the output of the monostable multivibrator remains high. As is readily known to those skilled in the art, adjustment of the output signal width of the circuit element 66 may be made such that the output constantly remains high so long as the square wave input is of at least a minimum preset frequency.

As shown, input leads 68,70 from the function generator 14 pass the sync signal from the function generator 14 to the counting circuit 18. In other words, on each cycle of the tester 12, resulting in one full flexure of the specimen 26 by one cycle of the lower bracket 30, there is one sync pulse output. Typically, this sync pulse occurs at the end of each cycle. The sync pulse is applied to the input of the monostable multivibrator 72 which acts as a "one-shot" to present an output pulse of fixed amplitude and duration upon receipt of the sync pulse. In other words, each cycle of the tester 12 is characterized by an output signal from the one-shot 72.

An AND gate 74 receives the pulse output of the monostable multivibrator 72 and the high level fixed output of the monostable vibrator 66. It should readily be apparent that the output of the multivibrator 62 is basically an enabling signal to the AND gate 74 which then passes the output pulses of the multivibrator 72 to the digital counter 76. Accordingly, the counter 76 receives a pulse on each cycle of the tester 12 so long as the specimen 26 of the associated station is unbroken.

When the specimen 26 breaks, the piezoelectric crystal 50 comes unloaded because its means of interconnection with the reciprocating lower bracket 30 is broken. Accordingly, the square wave output from the Schmidt trigger 64 terminates and the output of the monostable multivibrator 66 reverts to a low level and stays there. This low level inhibits the AND gate 74 and, accordingly, no further signals can pass therethrough to the digital counter 76. Accordingly, the digital counter 76 maintains therein a count equivalent to the number of cycles endured by the associated test specimen 26 prior to failure.

It should be readily appreciated that the instant invention may be implemented with a wide variety of testers and does not impede in any manner the testing of the elastomeric specimen itself. Further, there are no mechanical switches or the like to break or become inoperative.

Thus it can be seen that the objects of the invention have been satisfied by the structure presented hereinabove. While in accordance with the patent statutes only the best mode and preferred embodiment of the invention has been presented and described in detail, it is to be understood that the invention is not limited thereto or thereby. Accordingly, for an appreciation of the true scope and breadth of the invention reference should be had to the following claims.

I claim:

1. A cycle counter for testing elastomeric specimens, comprising:
 a stationary bracket;

a reciprocating bracket adapted for cyclic reciprocating movement toward and away from said stationary bracket;

first circuit means connected to said reciprocating bracket for controlling cycles of said reciprocating movement and presenting a first output signal at each such cycle;

a test specimen of elastomeric material interconnected between said stationary and reciprocating brackets, said test specimen being stretched by said reciprocating movement;

sensing means maintained at said stationary bracket and interconnected with said test specimen for generating a second output signal corresponding to a force applied thereto through said test specimen; and second circuit means connected to said first circuit means and said sensing means, receiving said first and second output signals, and determining therefrom the number of said cycles endured by said test specimen until failure thereof.

2. The cycle counter according to claim 1 wherein said sensing means comprises a piezoelecric crystal.

3. The cycle counter according to claim 2 wherein said piezoelectric crystal is maintained between first and second insulators, said first insulator being received by said stationary bracket.

4. The cycle counter according to claim 3 wherein said second insulator is operatively connected to said test specimen and adapted for relative movement with respect to said first insulator.

5. The cycle counter according to claim 4 wherein said relative movement is induced by said test specimen being flexed.

6. The cycle counter according to claim 2 wherein said second circuit means comprises a counter, said counter being activated by a coincidence of said first and second output signals.

7. The cycle counter according to claim 6 wherein said second circuit means further comprises a first monstable multivibrator receiving said second output signal and generating a fixed amplitude signal therefrom.

8. The cycle counter according to claim 7 wherein said second output signal is sinusoidal and wherein said second circuit means further comprises a squaring circuit interposed between said piezoelectric crystal and said first monstable multivibrator for receiving and squaring said sinusoidal second output signal.

9. The cycle counter according to claim 8 wherein said second circuit means further comprises a second monstable multivibrator receiving said first output signal and generating a pulse of fixed duration therefrom.

10. The cycle counter according to claim 9 wherein said second circuit means comprises a logic AND gate connected to said counter and receiving inputs from said first and second multivibrators.

11. Elastomeric testing apparatus, comprising:

a stationary member;

a reciprocating member;

a test specimen of elastomeric material interconnected between said stationary and reciprocating members, said test specimen cyclically stretched by reciprocating movement of said reciprocating member;

a piezoelectric crystal operatively connected to said test specimen and generating a first output signal as a function of said stretching of said reciprocating member;

circuit means receiving said first output signal and counting a number of cycles said test specimen is stretched until failure of said test specimen; and a control circuit connected to and controlling cycling of said reciprocating member and generating a sync pulse on each cycle thereof.

12. The elastomeric testing apparatus according to claim 11 wherein said circuit means comprises a counter activated by concurrence of said sync pulse and said first output signal.

13. The elastomeric testing apparatus according to claim 12 wherein said first output signal is of varying amplitude and wherein said circuit means includes a first multivibrator interposed between said piezoelectric crystal and said counter, said first multivibrator generating a fixed level signal in response to continued presence of said first output signal.

14. The elastomeric testing apparatus according to claim 13 wherein said circuit means further comprises a second multivibrator receiving said sync pulse and generating a fixed duration pulse therefrom.

15. The elastomeric testing apparatus according to claim 14 wherein said circuit means further comprises a logic AND gate connected to said counter and receiving said fixed level signal and fixed duration pulse as inputs thereto.

16. The elastomeric testing apparatus according to claim 11 wherein said piezoelectric crystal is maintained between first and second insulators at said stationary member, said first insulator adapted for movement relative to said second insulator.

17. The elastomeric testing apparatus according to claim 16 wherein said piezoelectric crystal is an annular disk.

* * * * *